(12) United States Patent
Takagi et al.

(10) Patent No.: US 7,557,227 B2
(45) Date of Patent: Jul. 7, 2009

(54) PROCESS FOR PRODUCING HEXAFLUOROPROPYLENE OXIDE

(75) Inventors: Hirokazu Takagi, Kanagawa (JP); Kazuya Oharu, Kanagawa (JP); Keiichi Ohnishi, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 1048 days.

(21) Appl. No.: 10/776,230

(22) Filed: Feb. 12, 2004

(65) Prior Publication Data

US 2005/0027132 A1      Feb. 3, 2005

(30) Foreign Application Priority Data

Feb. 17, 2003  (JP) .............................. 2003-038376

(51) Int. Cl.
*C07D 303/08*  (2006.01)
(52) U.S. Cl. .................. 549/550; 549/513; 549/563
(58) Field of Classification Search ................ 549/550, 549/513, 563
See application file for complete search history.

(56) References Cited

U.S. PATENT DOCUMENTS 3,358,003 A * 12/1967 Eleuterio et al. ............ 549/531
3,412,148 A    11/1968 Arbogast
4,287,128 A *  9/1981 Ratcliffe ..................... 549/523
4,288,376 A *  9/1981 Ohsaka et al. .............. 549/523

FOREIGN PATENT DOCUMENTS

| JP | 57-175185 | 10/1982 |
| JP | 3306957   | 7/2002  |

OTHER PUBLICATIONS

N. Ishikawa, Journal of synthetic organic chemistry Japan, pp. 131-137, vol. 35, No. 2, "The Chemistry of Hexafluoropropylene Oxide (HFPO)", Feb. 1977 (with English Abstract).

* cited by examiner

*Primary Examiner*—Janet L. Andres
*Assistant Examiner*—Raymond Covington
(74) *Attorney, Agent, or Firm*—Oblon, Spivak, McClelland, Maier & Neustadt, P.C.

(57) ABSTRACT

A process for producing hexafluoropropylene oxide, which comprises contacting a reaction product containing hexafluoropropylene oxide obtained by reacting hexafluoropropylene with oxygen, with at least one adsorbent selected from activated carbon and the following metal oxides, wherein the metal oxides are oxides of at least one metal selected from Groups 1 and 2 of the Periodic Table, Zr and Si.

31 Claims, No Drawings

PROCESS FOR PRODUCING HEXAFLUOROPROPYLENE OXIDE

BACKGROUND OF THE INVENTION

1. Field of the Invention

The present invention relates to a process for producing hexafluoropropylene oxide (hereinafter sometimes referred to simply as HFPO).

2. Discussion of Background

HFPO is a compound useful as a starting material monomer for fluorinated resins or rubbers, and it is produced industrially by an oxidation reaction of hexafluoropropylene (hereinafter referred to simply as HFP). HFPO contains, as impurities, unreacted HFP, water, hydrogen fluoride (hereinafter referred to simply as HF), hexafluoroacetone (hereinafter referred to simply as HFA), perfluoro acid fluorides such as perfluoropropionyl fluoride (hereinafter referred to simply as PFPF) and perfluoroacetyl fluoride, carbonyl fluoride, etc. These impurities include not only ones formed in the process for producing HFPO but also ones formed during the storage in a metal container.

Among the above-mentioned impurities, HFA and perfluoro acid fluorides act as chain transfer agents and thus hinder the polymerization reaction during the polymerization of HFPO. Further, water and HF also act as substances to hinder the polymerization reaction. Therefore, in a case where HFPO is used for a polymerization reaction, it is necessary to remove water, HF, HFA and perfluoro acid fluorides, contained as impurities, before its use.

As a method for removing water in HFPO, a method of passing HFPO through molecular sieves in a gas phase, is known (U.S. Pat. No. 3,412,148). Further, as a method for removing water, HF, HFA and perfluoro acid fluorides in HFPO, a method is known (JP-A-57-175185) wherein a metal hydroxide is packed at a preliminary stage and a metal hydride is packed in a subsequent stage, whereby HFPO is passed therethrough in a gas phase. On the other hand, a method is also known (Japanese Patent 3,306,957) wherein in order to prevent conversion from HFPO to HFA during the production or storage of HFPO, water or a water-containing compound is permitted to be present.

However, the above methods have various drawbacks. For example, in the method disclosed in U.S. Pat. No. 3,412,148, isomerization of HFPO to HFA is likely to take place by a catalytic activity of molecular sieves. Further, molecular sieves are likely to be fluorinated by HF, whereby not only the isomerization will be accelerated, but there will be a problem that decomposition of HFPO will proceed.

On the other hand, in the method disclosed in JP-A-57-175185, water will be produced as a by-product by the metal hydroxide at the preliminary stage, and in order to remove such water, it is required to combine the metal hydride at the subsequent stage, whereby not only the apparatus is required to be large sized to increase the installation costs, but also a labor is required to change packing materials for both the preliminary and subsequent stages. Further, the metal hydride is expensive, which makes the running cost high, and in addition, there is a drawback that hydrogen is produced as a by-product.

Further, in the method disclosed in Japanese Patent 3,306,957, HFPO and water are reacted to form a hydrate of pyruvic acid and HF, as disclosed by Nobuo Ishikawa in Organic Synthetic Chemistry Vol. 35, No. 2, p. 133 (1977). Formed HF will isomerizes HFPO to HFA as disclosed in JP-B-1-61090, and consequently there is a drawback that HFA will be increased.

SUMMARY OF THE INVENTION

It is an object of the present invention to solve such problems of the conventional methods and to provide a process for producing excellent hexafluoropropylene oxide containing little impurities such as water, hexafluoroacetone and hydrogen fluoride, which is advantageous also from the viewpoint of costs.

As a result of an extensive study, the present inventors have found that the above-mentioned problems can be solved by purifying a reaction product containing HFPO obtained by reacting HFP with oxygen, by means of a specific substance, and have finally accomplished the present invention.

Namely, the gist of the present invention resides in the following (1) to (10). In the present invention, "ppm" representing a quantity ratio shows "volume ppm (vol ppm)" which is a volume ratio, unless otherwise specified.

(1) A process for producing hexafluoropropylene oxide, which comprises contacting a reaction product containing hexafluoropropylene oxide obtained by reacting hexafluoropropylene with oxygen, with at least one adsorbent selected from activated carbon and the following metal oxides, wherein the metal oxides are oxides of at least one metal selected from Groups 1 and 2 of the Periodic Table, Zr and Si.

(2) The process according to (1), wherein the metal oxides are oxides of at least one metal selected from Mg, Ca, Zr and Si.

(3) The process according to (1), wherein the adsorbent is an adsorbent which does not substantially contain a transition metal oxide or aluminum oxide which acts as an isomerization catalyst for hexafluoropropylene oxide.

(4) The process according to (1), wherein the adsorbent is an adsorbent having a specific surface area of at least $10 \text{ m}^2/\text{g}$.

(5) The process according to (1), wherein the adsorbent is an adsorbent having adsorbed moisture preliminarily removed.

(6) The process according to (1), wherein the reaction product containing hexafluoropropylene oxide is contacted with the adsorbent in a gas phase.

(7) The process according to (1), wherein the reaction product containing hexafluoropropylene oxide obtained by reacting hexafluoropropylene with oxygen, is subjected to at least one pretreatment selected from distillation, alkali washing and dehydration treatment by means of a dehydrating agent, and the reaction product thus pretreated, is contacted with the adsorbent.

(8) The process according to (1) or (7), wherein the reaction product to be contacted with the adsorbent, contains at least one of hexafluoroacetone, hydrogen fluoride and moisture in an amount of at least 300 vol ppm.

(9) The process according to (8), wherein the reaction product to be contacted with the adsorbent, contains impurities to be removed by the adsorbent, in an amount of at most 5 vol %.

(10) The process according to (1) or (7), wherein purified hexafluoropropylene oxide is hexafluoropropylene oxide wherein the amount of moisture is at most 100 vol ppm, the amount of hexafluoroacetone is at most 100 vol ppm, and the amount of hydrogen fluoride is at most 100 vol ppm.

(11) The process according to (10), wherein purified hexafluoropropylene oxide is hexafluoropropylene oxide wherein the total amount of impurities is at most 200 vol ppm.

DETAILED DESCRIPTION OF THE PREFERRED EMBODIMENTS

On the surface of activated carbon or metal oxides to be used as an adsorbent in the present invention, hydroxyl groups are present in many cases. Such hydroxyl groups will serve as active points to adsorb and remove water, HF, HFA and perfluoro acid fluorides, and in a case where the adsorbent has adsorbed HF or perfluoro acid fluorides, they react with such hydroxyl groups to form water. However, activated carbon or a metal oxide in the present invention serves as a dehydrating agent to adsorb and remove the formed water, whereby it will be unnecessary to combine an expensive metal hydride at a subsequent stage. Further, the purification apparatus can be made to be small-sized, whereby the running cost and the installation cost can be reduced. Further, there will be no problem of production of hydrogen as a by-product.

The adsorbent is required to contain substantially no metal oxide component acting as an isomerization catalyst. As a metal oxide acting as an isomerization catalyst, an oxide of a transition metal such as Fe, Cr or Ni, or aluminum oxide may be mentioned. Accordingly, the adsorbent in the present invention is preferably an adsorbent which contains substantially no such a transition metal oxide or aluminum oxide.

Further, if an oxide of a transition metal such as Fe, Cr or Ni, an oxide having high acidity such as silica/alumina, alumina/titania, alumina/zirconia or alumina, is employed, isomerization of HFPO will take place. Especially, if such a metal oxide is fluorinated by HF and converted to a fluorinated metal oxide, the acidity will be high and, as disclosed in JP-A-58-62131, will act as a highly active isomerization catalyst. Whereas, the oxides of at least one metal selected from Groups 1 and 2 of the Periodic Table, Zr and Si, of the present invention, have no isomerization ability by themselves, and even if they are fluorinated by HF, the acidity will not be high, whereby isomerization of HFPO is believed to be suppressed.

Namely, as mentioned above, polymerization inhibiting substances such as HF, HFA, perfluoro acid fluorides, are contained in the reaction product containing HFPO obtained in the oxidation step of HFP, and in order to remove them, it is usually required to have a washing step by contact with an alkali, and a drying step by molecular sieves. However, in such removal method, water which can not be adsorbed by molecular sieves will remain, and further, there have been a problem that water and HFPO will react to form HF, and a problem that HFPO will be isomerized by molecular sieves to form HFA.

However, in the present invention, the purification treatment is carried out by means of the above-mentioned adsorbent, whereby it has been made possible to produce excellent HFPO having a very small content of water, HF and HFA.

According to the above-described process of the present invention, it is possible to obtain HFPO having a moisture content of preferably at most 100 ppm, more preferably at most 20 ppm. Further, according to the above-described process of the present invention, it is possible to obtain HFPO having a HFA amount of preferably at most 100 ppm, more preferably at most 20 ppm. Further, according to the above-described process of the present invention, it is possible to obtain HFPO having a HF amount of preferably at most 100 ppm, more preferably at most 20 ppm.

Particularly, according to the above-described process of the present invention, it is possible to obtain HFPO having a moisture amount of at most 100 ppm, a HFA amount of at most 100 ppm and a HF amount of at most 100 ppm. Especially, it is possible to obtain HFPO wherein the total amount of impurities to be removed by the adsorbent, including these three, is at most 200 ppm. Further, it is possible to obtain HFPO having a moisture amount of at most 20 ppm, a HFA amount of at most 20 ppm and a HF amount of at most 20 ppm. Especially, it is possible to obtain HFPO wherein the total amount of impurities to be removed by the adsorbent, including these three, is at most 100 ppm.

The process of the present invention is characterized by purifying the reaction product containing HFPO obtained by reacting HFP with oxygen, by treating it with at least one adsorbent selected from activated carbon and oxides of at least one metal selected from Groups 1 and 2 of the Periodic Table, Zr and Si.

The activated carbon which can be used in the process of the present invention, is not particularly limited. However, it is preferably one containing little metal component such as Fe, Cr, Ni or Al which accelerates isomerization of HFPO. As the activated carbon, one prepared from any one of wood, charcoal, fruit shell, coconut shell, peat, lignite, coal, etc. may be used. However, activated carbon obtainable from a vegetable material is preferred to one prepared from a mineral material. Particularly, coconut shell activated carbon is the most suitable activated carbon from the viewpoint of the specific surface area being high, metal impurities being little and the acid resistance being high.

The metal oxide which can be used as an adsorbent in the process of the present invention, is not particularly limited so long as it is an oxide of at least one metal selected from Groups 1 and 2 of the Periodic Table, Zr and Si. However, it is preferably an oxide of at least one metal selected from Mg, Ca, Zr and Si, and from the viewpoint of availability, price and efficiency for removal of impurities, an oxide of Si is particularly preferred.

Further, as a metal oxide which can be used in the present invention, it is also possible to use e.g. CaO/MgO, MgO/$ZrO_2$, MgO/$SiO_2$, CaO/$ZrO_2$, CaO/$SiO_2$, $SiO_2$/$ZrO_2$, $Na_2O$/$SiO_2$ or BaO/$SiO_2$, wherein an oxide of at least one metal selected from Groups 1 and 2 of the Periodic Table, Zr and Si is used as a carrier, and this carrier is impregnated with a solution having a salt of at least one metal selected from Groups 1 and 2 of the Periodic Table, Zr and Si, dissolved in water or an organic solvent, followed by drying and baking to have an oxide of at least one metal selected from Groups 1 and 2 of the Periodic Table, Zr and Si, supported thereon.

Further, it is also possible to employ a composite oxide such as CaO—MgO, MgO—$ZrO_2$, MgO—$SiO_2$, CaO—$ZrO_2$, CaO—$SiO_2$, $SiO_2$—$ZrO_2$, $SiO_2$—MgO—CaO, $Na_2O$—$SiO_2$ or BaO—$SiO_2$, prepared by coprecipitation from a solution having a salt of at least one metal selected from Groups 1 and 2 of the Periodic Table, Zr and Si, dissolved in water or an organic solvent.

From the viewpoint of the performance for removal of impurities, the specific surface area of the adsorbent useful in the present invention is preferably at least 10 $m^2$/g, more preferably at least 100 $m^2$/g, most preferably at least 300 $m^2$/g. The upper limit is not particularly limited, but it is usually 2,000 $m^2$/g. The specific surface area of the adsorbent in the present invention is a specific surface area obtained by a nitrogen adsorption method.

Further, the adsorbent useful in the present invention acts as a suitable dehydrating agent. Accordingly, if it is stored for a long period of time at room temperature, moisture in the air will be adsorbed on the surface, whereby the performance for removal of impurities may decrease. Accordingly, it is preferred to carry out moisture-removal treatment prior to using it for purification treatment, to make it in a state where the performance of removal of impurities is high. Namely, as an adsorbent useful in the present invention, it is preferred to employ activated carbon subjected to moisture removal treatment or a metal oxide subjected to moisture removal treatment.

As a method for moisture removal treatment, drying under reduced pressure (vacuum) or a method of feeding an inert gas may be mentioned. However, preferably, a method of feeding an inert gas containing substantially no moisture, particularly preferably nitrogen gas, may be employed.

The temperature for feeding the inert gas is not particularly limited so long as it is a temperature at which moisture removal treatment can be done. However, if it is too low, removal of moisture tends to be inadequate, and if it is too high, hydroxyl groups on the surface of the adsorbent will diminish, whereby the performance for removal of impurities may decrease. Accordingly, it is preferably from 50 to 250° C., particularly preferably from 80 to 150° C.

In the process of the present invention, the reaction product obtained in the oxidation step of HFP may directly be supplied to purification treatment by the adsorbent, or the reaction product may be subjected to suitable pretreatment and then supplied to purification treatment by the adsorbent. In a case where the amount of impurities in the reaction product is too much, the useful life of the adsorbent tends to be short, and frequent change of the adsorbent will be required, such being uneconomical. The reaction product immediately after obtained in the oxidation step of HFP, usually contains the reaction solvent and a large amount of acidic impurities. Accordingly, it is preferred that suitable pretreatment is carried out to reduce the amount of impurities to a certain level, and the reaction product thus treated is subjected to adsorption treatment of the present invention.

As such pretreatment, distillation, alkali washing or treatment by means of a dehydrating agent such as molecular sieves other than the above-mentioned adsorbent in the present invention, may, for example, be mentioned. These treatments may be used in combination. For example, in the case of distillation, it is possible to remove a certain amount of impurities, but it is difficult to sufficiently remove impurities having boiling points of the same level as HFPO, or impurities having boiling points lower than HFPO. For example, in the case of alkali washing, it is possible to remove impurities having high acidity, but it is difficult to remove HFA or moisture, and especially, in the case of washing by a aqueous alkali solution, moisture in HFPO will rather increase. For example, even if dehydration is carried out by molecular sieves after alkali washing, moisture may be removed, but HF, HFA, PFPF, etc. once removed by alkali washing will be formed anew, and their amount will increase. Accordingly, it is difficult to obtain HFPO having sufficiently little impurities, as intended by the present invention, solely by such pretreatments. Accordingly, it is preferred that impurities which can not adequately be removed by such pretreatments, are removed by the adsorption treatment of the present invention.

Especially in a case where a large amount of water is present in the reaction product even if distillation or pretreatment with an aqueous alkaline solution is carried out, it is preferred that even if HF or HFA will be formed anew, the reaction product is dried by molecular sieves and then, purification treatment by the present invention is carried out, whereby it is possible to obtain HFPO having higher purity after the purification treatment by the present invention.

The alkali washing is not particularly limited, and washing by an aqueous alkaline solution or an alkaline organic solvent, or washing by passing it through solid alkali may be mentioned. Washing by an aqueous alkaline solution is preferred. As the aqueous alkaline solution to be used for washing, an aqueous solution of KOH, NaOH, $K_2CO_3$ or $Na_2CO_3$ may, for example, be mentioned. From the viewpoint of the operation efficiency and the effect, an aqueous solution of KOH is particularly preferred.

By contacting the reaction product containing HFPO obtained by reacting HFP with oxygen, with an aqueous alkaline solution, HF, HFA, PFPF, etc. are removed, whereby a reaction product having little such impurities will be obtained. However, the moisture content will be substantially increased, and it will be necessary to remove such moisture. Accordingly, in order to dehydrate this reaction product without increasing HF, HFA, PFPF, etc., it is preferred to contact it with the above-mentioned adsorbent in the present invention to remove the moisture. HFPO obtainable by contacting such a reaction product having a large moisture content with the adsorbent in the present invention, is preferably HFPO having a moisture content of at most 100 ppm.

The reaction product to be contacted with the adsorbent of the present invention (including the reaction product after the above-mentioned pretreatment) is preferably a reaction product containing the component to be removed by the adsorbent, particularly at least one of HFA, HF and moisture, in an amount of at least 300 ppm, particularly at least 500 ppm. By the adsorption treatment of the present invention, it is possible to obtain purified HFPO wherein said component in an amount of at least 300 ppm, particularly at least 500 ppm, is made to be not more than 100 ppm.

The reaction product to be contacted with the adsorbent of the present invention is preferably at reaction product wherein based on HFPO, the HFA amount is at most 10 vol %, the HF amount is at most 10 vol %, and the moisture content is at most 20 vol %, and at least one of them is at least 300 ppm. Further, PFPF is preferably at most 10 vol %. Taking into consideration the useful life of the adsorbent and the purpose of the present invention, it is particularly preferably a reaction product wherein the HFA amount is at most 1 vol %, the HF amount is at most 1 vol %, and the water content is at most 2 vol % (further, in a case where PFPF is contained, it is at most 1 vol %), and at least one of them is at least 500 ppm. Further, the reaction product to be contacted with the adsorbent of the present invention is preferably a reaction product wherein the total amount of impurities including impurities other than the above-mentioned, is at most 20 vol %, particularly at most 5 vol %. Taking into consideration of the useful life of the adsorbent, it is most preferred that the total amount of impurities is at most 2 vol %. Here, the above-mentioned impurities are meant for acidic substances and organic substances to be removed by the adsorbent. Such impurities are not meant to be inert gasses such as nitrogen gas and unreacted HFP, and even if HFPO which is subjected to the adsorption treatment, contains an inert gas, such inert gas will not be taken into consideration in the calculation of the amount of impurities. Usually, HFPO which is subjected to the purification treatment, contains unreacted HFP as an inert gas.

Purified HFPO obtained by the purification treatment of the above reaction product with the adsorbent, is preferably HFPO wherein the HFA amount is at most 100 ppm and preferably HFPO wherein the HF amount is at most 100 ppm.

Further, it is preferably HFPO wherein the HFA amount is at most 100 ppm and the HF amount is at most 100 ppm. Further, even if the above reaction product is HFPO having a relatively small moisture content, the above purified HFPO is preferably HFPO having the moisture further removed, and its moisture content is preferably at most 100 ppm. The above purified HFPO is further preferably HFPO having PFPF removed, and the PFPF amount is preferably at most 100 ppm, particularly preferably at most 20 ppm.

In the present invention, the method for the purification treatment by the adsorbent is not particularly limited. Preferably, it is carried out by introducing HFPO continuously or in a batchwise into an adsorption tower packed with the adsorbent to let it contact in a gas phase or liquid phase.

The optimum contacting conditions are different between the gas phase method and the liquid phase method. In the case of the gas phase method, if the temperature of the adsorption tower is too low, HFPO is likely to be liquefied, and if it is too high, the performance for removal of impurities tends to decrease. Accordingly, it is preferably from 0 to 50° C., particularly preferably from 20 to 40° C.

The pressure of the adsorption tower is not particularly limited so long as it is a pressure under which HFPO will not be liquefied, and a reduced pressure to 1 MPa-G is suitably employed.

If the contact time in the adsorption tower is too short, the performance for removal of impurities will be inadequate, and if it is too long, the production efficiency will be poor. Accordingly, it is preferably from 0.5 to 30 minutes, particularly preferably from 1 to 10 minutes.

In the case of the liquid phase method, if the temperature of the adsorption tower is too low, a cooling machine having a high cooling power or dry ice will be required, and if it is too high, not only the performance for removal of impurities tends to decrease, but also a high pressure will be required to liquefy HFPO.

Accordingly, it is preferably from −70 to +30° C., particularly preferably from −30 to 0° C.

The pressure of the adsorption tower is not particularly limited so long as it is a pressure under which HFPO will be liquefied, and a reduced pressure to 1 MPa-G is suitably employed.

If the contact time in the adsorption tower is too short, the performance for removal of impurities tends to be inadequate, and if it is too long, the production efficiency will be poor. Accordingly, it is preferably from 1 to 100 hours, particularly preferably from 10 to 40 hours.

In the liquid phase method, the adsorbent is used preferably from 10 to 500 ml, more preferably from 50 to 200 ml, per 1,000 ml of HFPO.

Further, as compared with the liquid phase method, the gas phase method makes purification treatment in the vicinity of room temperature possible, whereby the electric power to be used for cooling, etc. may be small, and there is a merit such that the production efficiency is high, since the contact time is short. Accordingly, in the present invention, it is preferred to carry out purification treatment for the reaction product containing HFPO in a gas phase.

Now, specific embodiments of the present invention will be described with reference to Examples and Comparative Examples. However, it should be understood that the present invention is by no means restricted thereto.

EXAMPLE 1

100 ml of coconut shell activated carbon (specific surface area=900 m$^2$/g) was packed in an adsorption tower made of Inconel and having an internal diameter of 16 mm and a length of 1 m and heated to 100° C. by an oil bath, followed by drying for 24 hours by introducing nitrogen gas having a moisture content of at most 10 ppm thereto for a contact time of 10 seconds. 24 Hours later, it was confirmed that the moisture content in the nitrogen gas discharged was equal to or less than the moisture content in the dry nitrogen gas introduced. Thereafter, the adsorption tower was cooled and maintained at 30° C., and HFPO containing water, HF, HFA and PFPF as impurities, was introduced into the adsorption tower under normal pressure for a contact time of 3 minutes, to carry out the treatment. The treatment was carried out for 20 hours, and then, HFPO at the outlet of the adsorption tower was collected, whereupon moisture was analyzed by a dew point recorder, HF by a gas-detecting tube, and HFA and PFPF by $^{19}$F-NMR. Here, the above-mentioned HFPO containing impurities was HFPO obtained by distillation treatment of a reaction product obtained from the oxidation step of HFP.

EXAMPLE 2

The operation was carried out in the same manner as in Example 1 except that the coconut shell activated carbon in Example 1 was changed to MgO (specific surface area=120 m$^2$/g).

EXAMPLE 3

The operation was carried out in the same manner as in Example 1 except that the coconut shell activated carbon in Example 1 was changed to ZrO$_2$ (specific surface area=90 m$^2$/g).

EXAMPLE 4

The operation was carried out in the same manner as in Example 1 except that the coconut shell activated carbon in Example 1 was changed to a MgO—SiO$_2$ composite oxide prepared by a coprecipitation method (MgO/SiO$_2$ molar ratio=0.05, specific surface area=150 m$^2$/g).

EXAMPLE 5

The operation was carried out in the same manner as in Example 1 except that the coconut shell activated carbon in Example 1 was changed to silica gel (specific surface area=500 m$^2$/g).

EXAMPLE 6

Into a 1,000 ml autoclave, 100 ml of silica gel (specific surface area=500 m$^2$/g) was charged and heated to 100° C. by an oil bath, followed by drying for 24 hours by introducing nitrogen gas thereto for a contact time of 10 seconds. Thereafter, the autoclave was cooled and maintained at −20° C., 500 g of HFPO was introduced. Upon expiration of 20 hours, HFPO in the autoclave was collected, and the analyses were carried out by the same methods as in Example 1.

COMPARATIVE EXAMPLE 1

The operation was carried out in the same manner as in Example 1 except that the coconut shell activated carbon in Example 1 was changed to molecular sieves (specific surface area=100 m$^2$/g).

The results of Examples 1 to 6 and Comparative Example 1 are shown in Table 1.

TABLE 1

Concentrations of impurities in HFPO before and after purification treatment

| | | Concentrations of impurities in HFPO (vol ppm) | | | |
|---|---|---|---|---|---|
| | | Water | HF | HFA | PFPF |
| Before purification | | 210 | 1,500 | 2,200 | 1,450 |
| After purification | Ex. 1 | 30 | 15 | 20 | 0 |
| | Ex. 2 | 20 | 1 | 20 | 0 |
| | Ex. 3 | 15 | 20 | 10 | 0 |
| | Ex. 4 | 5 | 10 | 0 | 0 |
| | Ex. 5 | 5 | 5 | 0 | 0 |
| | Ex. 6 | 8 | 15 | 0 | 0 |
| | Comp. Ex. 1 | 50 | 1,530 | 6,800 | 7,200 |

EXAMPLE 7

The operation was carried out in the same manner as in Example 1 except that in Example 1, the coconut shell activated carbon was changed to silica gel (specific surface area=500 m$^2$/g), and HFPO obtained by further washing the same HFPO containing impurities, as used in Examples 1 to 6, with alkaline water, was used. The results are shown in Table 2.

TABLE 2

Concentrations of impurities in HFPO before and after purification treatment

| | Concentrations of impurities in HFPO (vol ppm) | | | |
|---|---|---|---|---|
| | Water | HF | HFA | PFPF |
| Before purification | 8,500 | 0 | 0 | 0 |
| After purification | 90 | 0 | 0 | 0 |

In the present invention, the reaction product containing HFPO obtained by reacting HFP with oxygen, is treated for purification by using at least one adsorbent selected from activated carbon and oxides of at least one metal selected from Groups 1 and 2 of the Periodic Table, Zr and Si, whereby it is possible to produce HFPO of high purify, and downsizing of the installation for purification is made possible, whereby the running cost and the installation cost may be reduced. Further, there will be no such a problem as production of hydrogen as a by-product.

The entire disclosure of Japanese Patent Application No. 2003-038376 filed on Feb. 17, 2003 including specification, claims and summary is incorporated herein by reference in its entirety.

What is claimed is:

1. A process for purifying hexafluoropropylene oxide, which comprises:
  contacting a reaction product containing hexafluoropropylene oxide obtained by reacting hexafluoropropylene with oxygen, with at least one adsorbent selected from the group consisting of activated carbon, a Group 1 metal oxide, a Group 2 metal oxide, an oxide of Zr and an oxide of Si, wherein the contacting is carried out at a temperature of from −70 to 50° C.

2. The process according to claim 1, wherein the adsorbent is an activated carbon derived from a vegetable material.

3. The process according to claim 1, wherein the adsorbent is a metal oxide of at least one metal selected from the group consisting of Mg, Ca, Zr and Si.

4. The process according to claim 1, wherein the adsorbent is an adsorbent which does not substantially contain a transition metal oxide or aluminum oxide which acts as an isomerization catalyst for hexafluoropropylene oxide.

5. The process according to claim 1, wherein the adsorbent is an adsorbent having a specific surface area of at least 10 m$^2$/g.

6. The process according to claim 1, wherein the adsorbent is activated carbon having a specific surface area of at least 10 m$^2$/g.

7. The process according to claim 1, wherein the adsorbent is made of an oxide of at least one metal selected from the group consisting of Mg, Ca, Zr and Si, and has a specific surface area of at least 10 m$^2$/g.

8. The process according to claim 1, wherein the adsorbent is an adsorbent having adsorbed moisture preliminarily removed.

9. The process according to claim 8, wherein the adsorbent having adsorbed moisture preliminarily removed, is an adsorbent having the moisture removed by feeding an inert gas which contains substantially no moisture.

10. The process according to claim 1, wherein the reaction product containing hexafluoropropylene oxide is contacted with the adsorbent in a gas phase.

11. The process according to claim 1, wherein the reaction product containing hexafluoropropylene oxide obtained by reacting hexafluoropropylene with oxygen, is subjected to at least one pretreatment selected from distillation, alkali washing and dehydration treatment by means of a dehydrating agent, and the reaction product thus pretreated, is contacted with the adsorbent.

12. The process according to claim 11, wherein the dehydrating agent is molecular sieves.

13. The process according to claim 1, wherein the reaction product to be contacted with the adsorbent, contains at least one of hexafluoroacetone, hydrogen fluoride and moisture in an amount of at least 300 vol ppm.

14. The process according to claim 13, wherein the reaction product to be contacted with the adsorbent, contains impurities to be removed by the adsorbent, in an amount of at most 5 vol %.

15. The process according to claim 1, wherein the reaction product to be contacted with the adsorbent, contains at least one of hexafluoroacetone, hydrogen fluoride and moisture in an amount of at least 500 vol ppm, and purified hexafluoropropylene oxide is hexafluoropropylene oxide wherein the component in an amount of at least 500 vol ppm is not more than 100 vol ppm.

16. The process according to claim 15, wherein the reaction product to be contacted with the adsorbent, contains impurities to be removed by the adsorbent, in an amount of at most 2 vol %.

17. The process according to claim 1, wherein, after the contacting, the hexafluoropropylene oxide has an amount of moisture of at most 100 vol ppm, an amount of hexafluoroacetone of at most 100 vol ppm, and an amount of hydrogen fluoride of at most 100 vol ppm.

18. The process according to claim 17, wherein, after the contacting, the hexafluoropropylene oxide has a total amount of impurities of at most 200 vol ppm.

19. The process according to claim 1, wherein, after the contacting, the hexafluoropropylene oxide has an amount of moisture of at most 20 vol ppm, an amount of hexafluoroacetone of at most 20 vol ppm, and an amount of hydrogen fluoride of at most 20 vol ppm.

20. The process according to claim 19, wherein, after the contacting, the hexafluoropropylene oxide has a total amount of impurities of at most 100 vol ppm.

21. The process according to claim 11, wherein the reaction product to be contacted with the adsorbent, contains at least one of hexafluoroacetone, hydrogen fluoride and moisture in an amount of at least 300 vol ppm.

22. The process according to claim 21, wherein the reaction product to be contacted with the adsorbent, contains impurities to be removed by the adsorbent, in an amount of at most 5 vol %.

23. The process according to claim 11, wherein the hexafluoropropylene oxide, contains at least one component selected from the group consisting of hexafluoroacetone, hydrogen fluoride and moisture in an amount of at least 500 vol ppm before the contacting, and after the contacting, the amount of the components in an amount of at least 500 vol ppm of the hexafluoropropylene oxide is not more than 100 vol ppm.

24. The process according to claim 23, wherein the reaction product to be contacted with the adsorbent, contains impurities to be removed by the adsorbent, in an amount of at most 2 vol %.

25. The process according to claim 11, wherein, after the contacting, the hexafluoropropylene oxide has an amount of moisture of at most 100 vol ppm, an amount of hexafluoroacetone of at most 100 vol ppm, and an amount of hydrogen fluoride of at most 100 vol ppm.

26. The process according to claim 25, wherein, after the contacting, the hexafluoropropylene oxide has an amount of impurities of at most 200 vol ppm.

27. The process of claim 1, which is a process for purifying hexafluoropropylene oxide.

28. Hexafluoropropylene oxide produced with the process of claim 1.

29. The process of claim 1, wherein the contacting is carried out at a temperature of from −30 to 400° C.

30. The process of claim 1, wherein the adsorbent is at least one selected from the group consisting of MgO, $ZrO_2$, a $MgOSiO_2$ composite oxide, and a silica gel.

31. The process of claim 1, wherein during the contacting, hexafluoropropylene is an inert gas.

* * * * *